(12) United States Patent
Donahoe et al.

(10) Patent No.: US 8,771,285 B2
(45) Date of Patent: Jul. 8, 2014

(54) DRIVE TOOL FOR ORTHOPEDIC SCREWS

(75) Inventors: Ryan M. Donahoe, San Diego, CA (US); James I. Johnson, Temecula, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 1162 days.

(21) Appl. No.: 11/532,291

(22) Filed: Sep. 15, 2006

(65) Prior Publication Data

US 2008/0097458 A1    Apr. 24, 2008

(51) Int. Cl.
*A61B 17/58* (2006.01)
*A61C 8/00* (2006.01)
*B25B 13/00* (2006.01)

(52) U.S. Cl.
USPC .............................. 606/104; 433/174; 81/52

(58) Field of Classification Search
USPC .......... 606/86 A, 99, 100, 104; 433/165, 141, 433/172, 173, 174, 175, 176, 202.1, 163; 81/121.1, 124.2, 122, 124.6, 125, 81/176.1; D8/29
See application file for complete search history.

(56) References Cited

U.S. PATENT DOCUMENTS

| | | | | |
|---|---|---|---|---|
| 916,951 | A | * | 3/1909 | Jeffrey .............................. 81/119 |
| 1,321,776 | A | * | 11/1919 | Stepanian .................... 81/124.2 |
| 1,346,061 | A | * | 7/1920 | Rosenberg ........................ 81/185 |
| 4,258,596 | A | * | 3/1981 | Bisbing et al. ................... 81/436 |
| 4,380,942 | A | * | 4/1983 | Fenton ............................. 81/436 |
| 4,955,811 | A | | 9/1990 | Lazzara et al. |
| 5,009,596 | A | | 4/1991 | Soderberg |
| 5,065,649 | A | | 11/1991 | Evers et al. |
| 5,074,174 | A | * | 12/1991 | Kim ................................. 81/185 |
| 5,171,117 | A | * | 12/1992 | Seidl ............................. 411/404 |
| 5,269,208 | A | | 12/1993 | Kolvites et al. |
| 5,484,440 | A | | 1/1996 | Allard |
| 5,538,428 | A | | 7/1996 | Staubli |

(Continued)

FOREIGN PATENT DOCUMENTS

GB    2141803    1/1985

OTHER PUBLICATIONS

Product Brochure, Sulzer Medica Sulzer Calcitek Inc., Spline Dental Implant Interface, 2000.

(Continued)

*Primary Examiner* — Christian Sevilla
(74) *Attorney, Agent, or Firm* — Schwegman Lundberg & Woessner, P.A.

(57) ABSTRACT

A drive tool for accepting and rotationally locking the head portion of an orthopedic screw, such as a dental implant, to impart driving torque to the screw. In one exemplary embodiment, the drive tool includes an elongate body having an opening at its proximal end which is sized to receive the head portions of at least two different dental implants, the head portions of the dental implants being oriented at different angles with respect to the implant body portions. When the head portion of an implant is received within the opening, the drive tool is rotationally locked with respect to the implant. In this position, the body of the drive tool remains oriented so that same is substantially colinear with the body portion of the implant. Although the invention is described in the context of a drive tool used with a dental implant having a body portion and a head portion or abutment portion, the invention is more broadly applicable to drive tools which may be used with other types of orthopedic screws.

16 Claims, 5 Drawing Sheets

(56) References Cited

U.S. PATENT DOCUMENTS

| | | | |
|---|---|---|---|
| 5,636,990 A * | 6/1997 | Stemmann | 433/189 |
| 5,643,320 A | 7/1997 | Lower et al. | |
| 5,690,489 A | 11/1997 | Carchidi | |
| 5,755,575 A | 5/1998 | Biggs | |
| 5,927,979 A | 7/1999 | Misch et al. | |
| 5,944,525 A * | 8/1999 | Ura | 433/173 |
| 5,974,917 A | 11/1999 | Way | |
| 6,158,310 A * | 12/2000 | Goss et al. | 81/121.1 |
| 6,159,008 A | 12/2000 | Kumar | |
| 6,247,933 B1 | 6/2001 | Wagner et al. | |
| 6,314,841 B1 * | 11/2001 | Burk et al. | 81/125.1 |
| 6,315,562 B1 | 11/2001 | Kumar | |
| 6,343,531 B2 | 2/2002 | Amis | |
| 6,389,934 B1 | 5/2002 | Yen | |
| 6,416,324 B1 | 7/2002 | Day | |
| 6,454,567 B1 | 9/2002 | Carchidi et al. | |
| 6,502,483 B1 * | 1/2003 | Swank et al. | 81/437 |
| 6,827,575 B1 | 12/2004 | Jorneus | |
| 2003/0054318 A1 | 3/2003 | Gervais et al. | |
| 2003/0054319 A1 | 3/2003 | Gervais et al. | |
| 2003/0224327 A1 | 12/2003 | Costantino | |
| 2004/0101807 A1 * | 5/2004 | Porter et al. | 433/173 |
| 2004/0137406 A1 * | 7/2004 | Kennard | 433/174 |
| 2004/0175673 A1 * | 9/2004 | Zickman et al. | 433/173 |
| 2007/0082320 A1 * | 4/2007 | Faus Badia | 433/173 |

OTHER PUBLICATIONS

Product Catalog, Swede-Vent, The external hex system from Dentsply, Dentsply Implant, 1992.

* cited by examiner

DRIVE TOOL FOR ORTHOPEDIC SCREWS

BACKGROUND OF THE INVENTION

1. Field of the Invention

The present invention relates to a drive tool for orthopedic screws such as dental implants.

2. Description of the Related Art

Dental implants are commonly used as anchoring members in prosthodontic restorations to provide prosthetic teeth at one or more edentulous sites in a patient's dentition at which the patient's original natural teeth have been lost or damaged. Typically, known implant systems include a dental implant made from a suitable biocompatible material, such as titanium. The dental implant is typically threaded into a bore which is drilled into the patient's mandible or maxilla at the edentulous site. The implant body provides an anchoring member for a dental abutment, which in turn provides an interface between the implant and a dental restoration. The restoration is typically a porcelain crown fashioned according to known methods to replicate the shape of the tool being replaced. Additionally, some dental implant systems utilize an implant which incorporates the implant and abutment into an integral implant forming a single, unitary body.

To thread a dental implant into the maxilla or mandible of a patient, a drive tool may be used. A drive tool typically accepts the head portion, or abutment portion, of the dental implant and rotationally locks the head portion with respect to the drive tool. This rotational locking can be accomplished by either an external or internal feature on the drive tool which mates with a corresponding feature on the dental implant and allows for the drive tool to impart rotational force to the head portion of the dental implant. Dental implants are often constructed to have the head portion, or abutment portion, of the implant angled with respect to the implant body to properly fit the anatomy of a patient's dentition, and what is needed is an improved drive tool to accommodate such implants.

SUMMARY OF THE INVENTION

The present invention provides a drive tool for accepting and rotationally locking the head portion of an orthopedic screw, such as a dental implant, to impart driving torque to the screw. In one exemplary embodiment, the drive tool includes an elongate body having an opening at its proximal end which is sized to receive the head portions of at least two different dental implants, the head portions of the dental implants being oriented at different angles with respect to the implant body portions. When the head portion of an implant is received within the opening, the drive tool is rotationally locked with respect to the implant. In this position, the body of the drive tool remains oriented so that same is substantially colinear with the body portion of the implant. Although the invention is described in the context of a drive tool used with a dental implant having a body portion and a head portion or abutment portion, the invention is more broadly applicable to drive tools which may be used with other types of orthopedic screws.

In one exemplary embodiment, the drive tool includes a passageway in communication with the opening at the proximal end of the drive tool. The passageway terminates at an opening formed in the outer surface of the elongate body of the drive tool. When the head portion of an implant is seated within the drive tool, the head portion of the implant can be accepted by the passageway and can extend to or through the opening in the outer surface of the drive tool. In this manner, the drive tool can accommodate at least two types of implants having head portions of varying angles.

Thus, advantageously, the present invention allows for a single drive tool to mate with implants having head portions with different angular orientations with respect to the implant body portions, such that only one drive tool may be used for multiple different implants. Furthermore, the incorporation of the radial opening allows for the drive tool of the present invention to be substantially the same size as known drive tools that accept only a single type of implant.

In one form thereof, the present invention provides a drive tool for selectively driving one of a pair of orthopedic screws, a first one of the orthopedic screws having a threaded body portion and a first head portion extending from the threaded body portion, the first head portion forming a first angle with the threaded body portion of the first orthopedic screw, a second of the orthopedic screws having a threaded body portion and a second head portion extending from the threaded body portion of the second orthopedic screw and forming a second angle with the threaded body portion of the second orthopedic screw, the first angle not equal to the second angle, the drive tool including an elongate body having a first end, the first end having a first opening defining a cavity, the cavity sized to receive the head portion of the first orthopedic screw and rotationally lock the first orthopedic screw to the elongate body, whereby relative rotation between the first orthopedic screw and the elongate body is substantially prohibited when the head portion of the first orthopedic screw is positioned in the cavity, the cavity further sized to receive the head portion of the second orthopedic screw and rotationally lock the second orthopedic screw to the elongate body, whereby relative rotation between the second orthopedic screw and the elongate body is substantially prohibited when the head portion of the second orthopedic screw is positioned in the cavity.

In another form thereof, the present invention provides a drive tool for use in rotatably driving one of at least two orthopedic screws having head portions divergent from one another, the drive tool including a body defining a longitudinal axis; a drive fitting on the body; and a cavity at a proximal end of the body, the cavity comprising: a first portion substantially aligned with the longitudinal axis; a second portion radially offset from the first portion with respect to the longitudinal axis; and non-rotational engagement structure cooperable with each of the first and second portions.

In another form thereof, the present invention provides a drive tool including a body, a cavity defined within a proximal end of the body, the cavity including a plurality of walls dividing the cavity into a plurality of discrete sections of decreasing volume from the proximal end of the body towards a distal end of the body.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrates preferred embodiments of the invention, in one form, and such exemplification is not to be construed as limiting the scope of the invention any manner.

DETAILED DESCRIPTION

Figure 1:
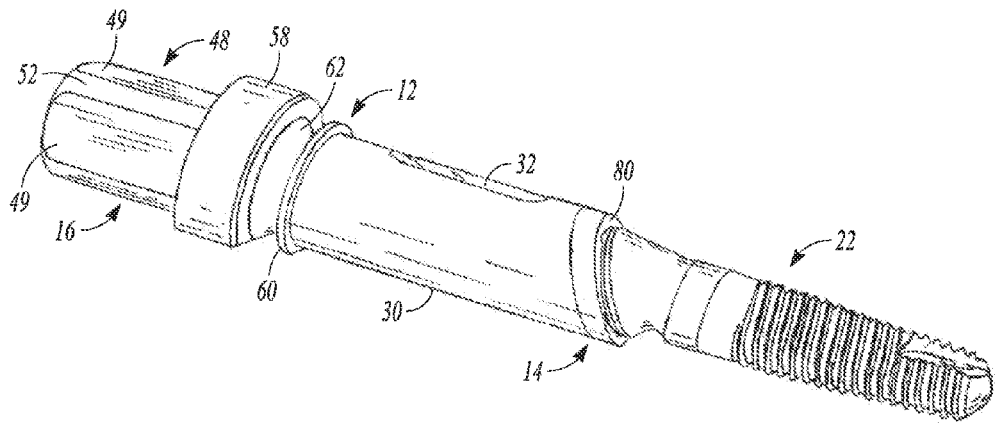
FIG. 1 is a perspective view of the drive tool drivingly connected to an implant, shown as a dental implant.
Figure 2:
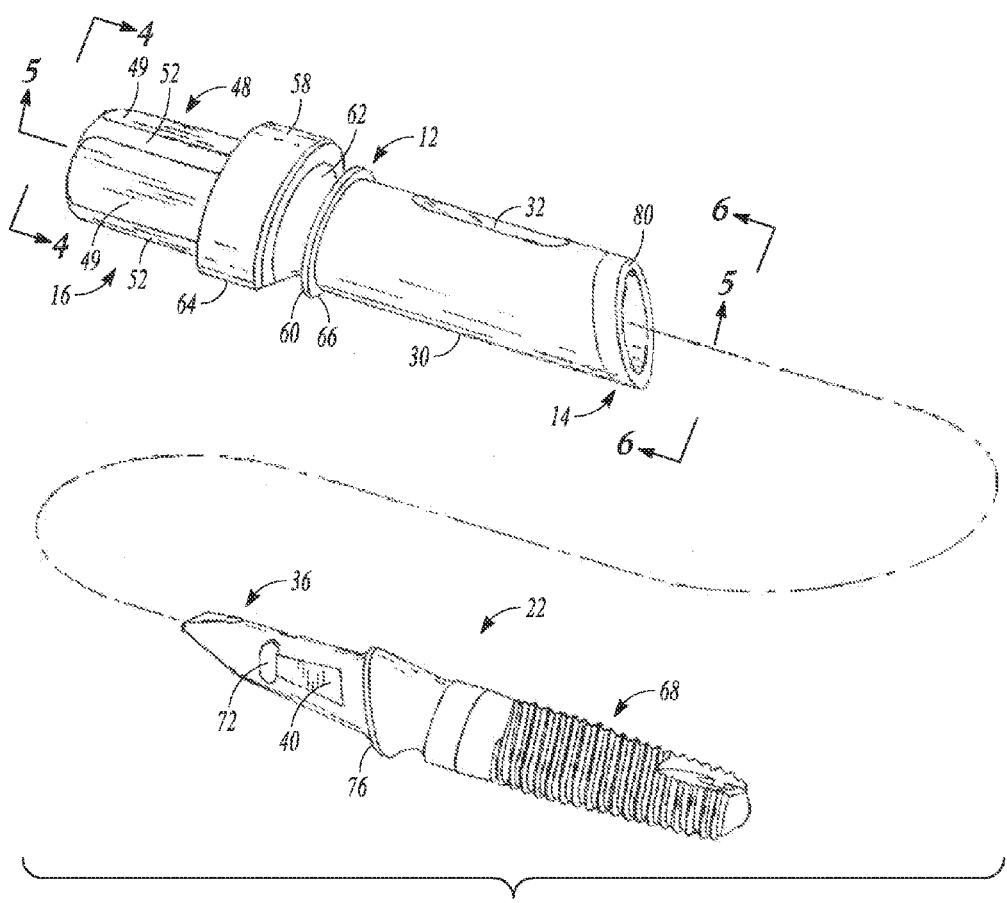
FIG. 2 is an exploded perspective view of the drive tool and dental implant of FIG. 1.
Figure 3:
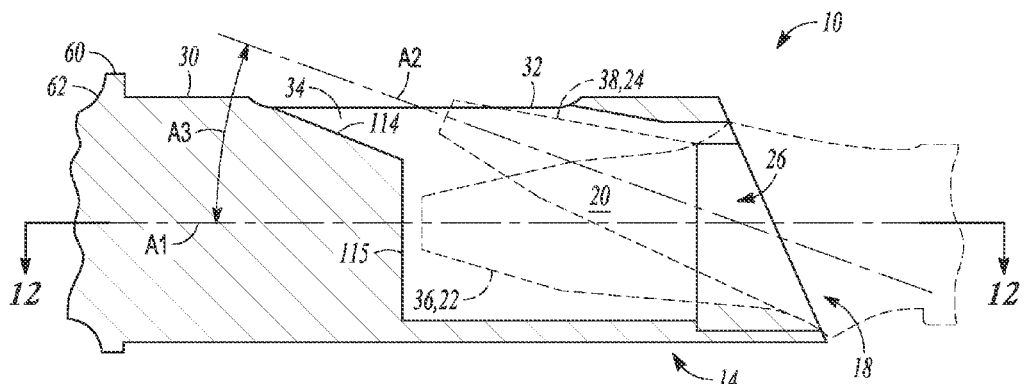
FIG. 3 is a fragmentary cross-sectional view of the drive tool of FIG. 1.

FIGS. 1-3 show drive tool 10 according to one embodiment of the present invention, including an elongate body 12 having proximal end 14 and distal end 16. As used herein, proximal and distal mean closest to and furthest from a patient's maxilla or mandible, respectively, during use of drive tool 10. Proximal end 14 of drive tool 10 includes opening 18 which defines a cavity 20, shown in FIGS. 2 and 3. Cavity 20 is sized to accept orthopedic screws such as dental implants 22 and 24, shown in FIGS. 10 and 11, respectively, each of which include a body portion and a head or abutment portion. Although the drive tools disclosed herein are described in the context of use with dental implants, the drive tools may also find application with other types of orthopedic screws, such as internal or external fixation screws in trauma systems, and pedicle screws in spinal systems, for example.

Figure 6:
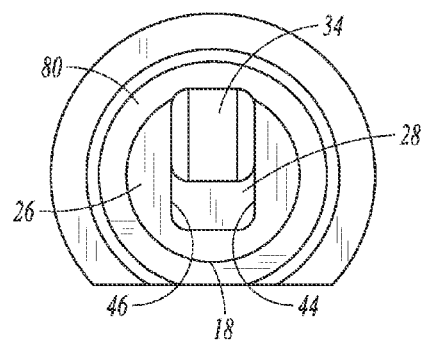
FIG. 6 is an end view of the proximal end of the drive tool of FIGS. 1 and 2.

In an exemplary embodiment, referring to FIGS. 3 and 6, cavity 20 of elongate body 12 is divided into two portions, proximal portion 26 and distal portion 28. Additionally, outer surface 30 of drive tool 10 includes radial opening 32. Radial opening 32 defines passageway 34 which is angled to intersect cavity 20 at distal portion 28 of cavity 20 to provide a clearance space for receipt of certain angled orthopedic screws as described below. Passageway 34 and cavity 20 may also include internal surfaces which substantially correspond to the external profiles of head portions 36 and 38 of dental implants 22 and 24, shown in FIGS. 10 and 11 and described in further detail below. Cavity 20 also includes non-rotational engagement structure, such as flat drive surfaces 44 and 46, which engage corresponding non-rotational structure of implants 22 and 24, such as flat portions 40 and 42 thereof, respectively, thereby rotationally locking and substantially prohibiting relative rotational motion between drive tool 10 and dental implants 22 and 24, as described below.

Figure 4:
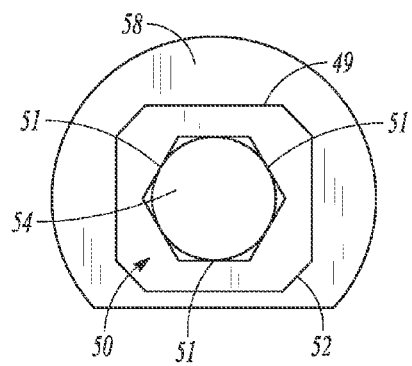
FIG. 4 is an end view of the distal end of the drive tool of FIGS. 1 and 2.

As depicted in FIGS. 1, 2, and 4, distal end 16 of drive tool 10 may include one or more drive fittings, such as external polygonal fitting 48, which in one embodiment includes four substantially flat walls 49 together defining a square cross-section, and internal polygonal fitting 50, which in one embodiment includes six substantially flat walls 51 together defining a hexagonal cross-section. The number of walls of external polygonal fitting 48 and internal polygonal fitting 50 may be varied. External polygonal fitting 48 may be engaged by a driving instrument (not shown), such as a ratchet wrench or a drill, for example, to apply rotational torque to drive tool 10. External polygonal fitting 48 includes curved surfaces 52 between adjacent walls 49 thereof, which facilitate the engagement of the driving instrument with drive tool 10. Internal polygonal fitting 50 also includes broach relief 56, which facilitates the manufacture of cavity 54 by accepting an accumulation of debris during broaching of cavity 54. Internal polygonal fitting 50 is capable of accepting a different type of driving instrument than internal polygonal fitting 48 to apply driving torque to drive tool 10.

As shown in FIGS. 1 and 2, annular collar 58 is disposed adjacent to polygonal fitting 48, which, together with annular flange 60, forms the sidewalls of an annular groove 62 which facilitates handling and manipulation of drive tool 10. Annular collar 58 and annular flange 60 include flat sections 64, 66, respectively, which provide a visual indication to the surgeon when drive tool 10 is correctly aligned with dental implants 22 and 24.

Figure 10:
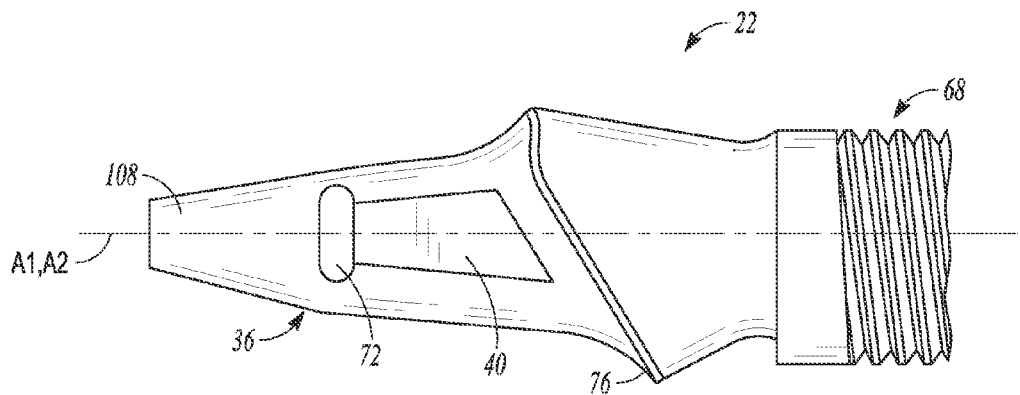
FIG. 10 is a side elevation view of a portion of a one-piece dental implant with a substantially coliner orientation between the abutment portion and the implant body portion.
Figure 11:
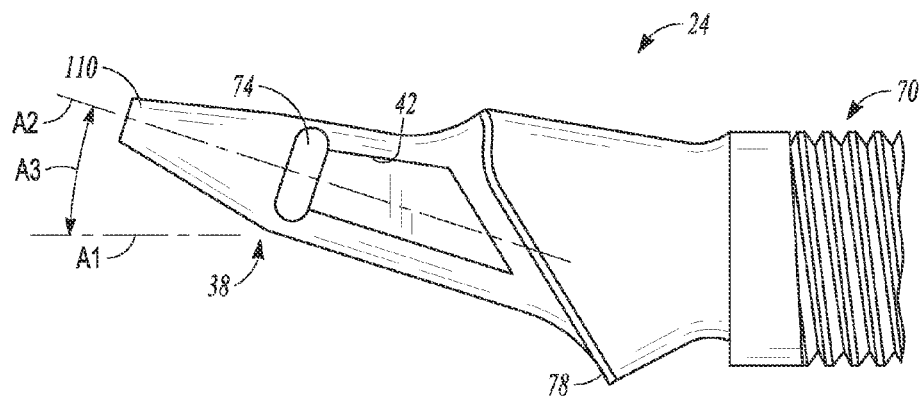
FIG. 11 is a side elevation view of a portion of a one-piece dental implant with a substantially non-colinear, or angled, orientation between the abutment portion and the implant body portion.

FIGS. 10 and 11 show exemplary embodiments of dental implants 22 and 24 having body portions 68 and 70 and abutment portions or head portions 36 and 38, respectively, which are receivable within opening 18 of drive tool 10. Body portions 68 and 70, partially shown in FIGS. 10 and 11, are externally threaded to facilitate implantation in the mandible or maxilla. Head portions 36 and 38 include channels 72 and 74 and flat portions 40 and 42, respectively. Channels 72 and 74 are configured for receipt of a coping (not shown) to allow a dentist to take impressions in order to create a dental restoration.

Dental implants 22 and 24 also include margins 76 and 78 which may abut annular rim 80 of drive tool 10 when head portions 36 and 38 of implants 22 and 24, respectively, are received within cavity 20 of drive tool 10. In one exemplary embodiment, shown in FIG. 1, margins 76 and 78 and annular rim 80 are separated by a small distance, such as 0.25 inches, for example. As shown in FIG. 10, head portion 36 of implant 22 is non-angled, or has an angle of 0°, wherein head portion 36 includes a longitudinal axis $A_2$ which is substantially colinear with longitudinal axis $A_1$ of body portion 68. By contrast, as shown in FIG. 11, head portion 38 of implant 24 is angled, wherein head portion 38 includes a longitudinal axis $A_2$ which is angled with respect to, or divergent from, longitudinal axis A1 of body portion 70 by an angle $A_3$.

In use, flat portions 40 and 42 are engaged by drive surfaces 44 and 46 of drive tool 10 upon insertion of head portions 36 and 38 into cavity 20 of drive tool 10, substantially prohibiting relative rotation between dental implants 22 and 24 and drive tool 10 and thereby allowing rotational torque to be imparted to implants 22 and 24 via drive tool 10. Advantageously, the non-rotational engagement structure of drive tool 10 allows for substantial. prohibition of relative rotation between drive tool 10 and implants which have heads with different angular orientations with respect to the implant bodies, such as implants 22 and 24. As shown in FIG. 3, the end of head portion 38 of implant 24 may be accommodated within channel 34 of cavity 20 of drive tool 10. FIG. 3 also depicts the longitudinal axis A1 of the body of implants 22 and 24, and the axis A2 of the head portion 38 of implant 24. A2 diverges from A1 by acute angle A3. The axes of the cavity 20 and channel 34 generally correspond to the axes of the implants 22 and 24. FIG. 3 also illustrates a wall 114 extending from a coronal wall 115 of cavity 20. The wall 114 extends outwardly from Axis A1 generally at an angle corresponding to acute angle A3 to accommodate angled head portion 38.

Figure 5:
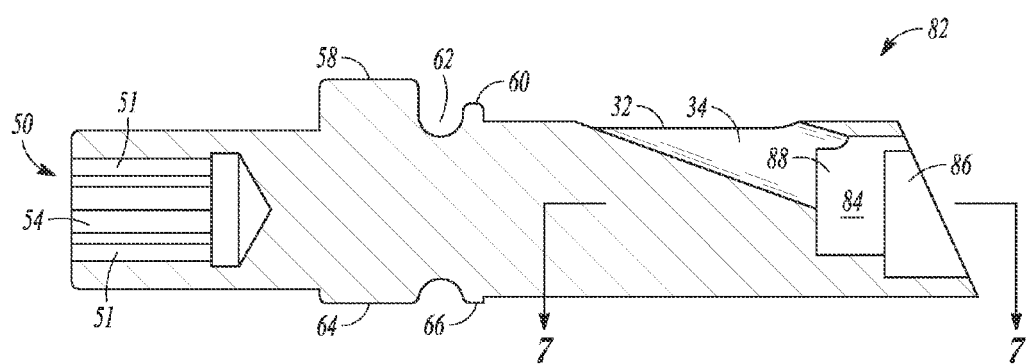
FIG. 5 is a longitudinal cross-sectional view of a drive tool according to another embodiment.
Figure 7:
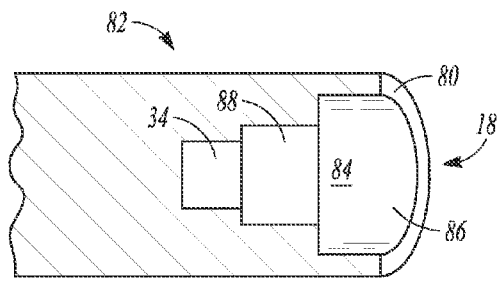
FIG. 7 is a fragmentary cross-sectional view of the drive tool of FIG. 5.

FIGS. 5 and 7 depict drive tool 82 according to another embodiment. Except as described below, drive tool 82 of FIGS. 5 and 7 is substantially identical to drive tool 10 of FIGS. 1-3 discussed above, and identical reference numerals will be used to designate identical or substantially identical features therebetween. Proximal end 14 of elongate body 12 of drive tool 82 has opening 18 defining cavity 84, which may include drive surfaces, such as drive surfaces 44 and 46 of drive tool 10 for engaging corresponding drive surfaces of the dental implants. Cavity 84 is divided into two portions, proximal portion 86 and distal portion 88. Outer diameter 30 includes radial opening 32 defining passageway 34, which intersects cavity 84 at distal portion 88. The design of cavity 84 allows for drive tool 78 to accept orthopedic screws having an angled head portion substantially non-colinear with the body portion thereof, such as dental implant 24 described above, for example. Portions 86, 88 of cavity 84 define a substantially lesser volume than portions 26, 28 of drive tool 10. In this manner, opening 18 defines an interior configuration of cavity 84 which is dimensioned to closely receive head portion 38 of implant 24 to closely maintain the alignment and positioning of head portion 36 of implant 24 within cavity 84.

Figure 8:
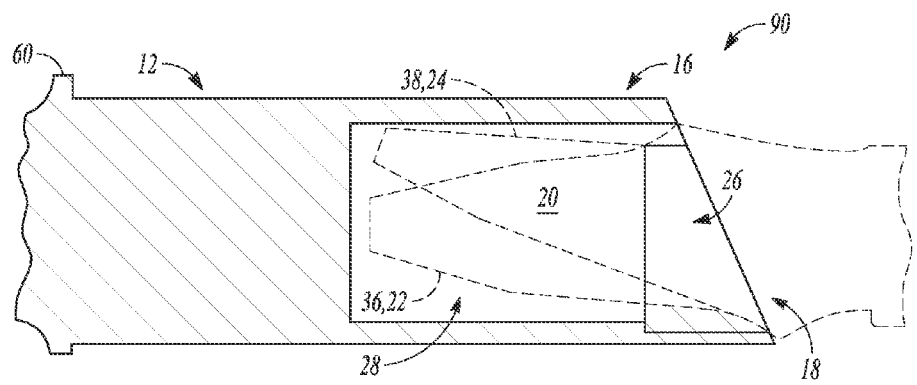
FIG. 8 is a fragmentary cross-sectional view of a drive tool according to a further embodiment.

FIG. 8 depicts drive tool 90 according to another embodiment. Except as described below, drive tool 90 of FIG. 8 is substantially identical to drive tool 82 of FIGS. 1-3 discussed above, and identical reference numerals will be used to designate identical or substantially identical features therebetween. Drive tool 90 has proximal end 14 having opening 18 defining cavity 84, which may include drive surfaces, such as drive surfaces 44 and 46 of drive tool 10, for engaging corresponding drive surfaces of the dental implants. Drive tool 90 is identical to drive tool 10, shown in FIGS. 1-3, except for the absence of radial opening 32 and passageway 34, wherein drive tool 90 may accept implants having head portions within a more limited range of angular orientations with respect to the body portions of the implants than the implants which may be accepted by drive tool 10.

Figure 9:
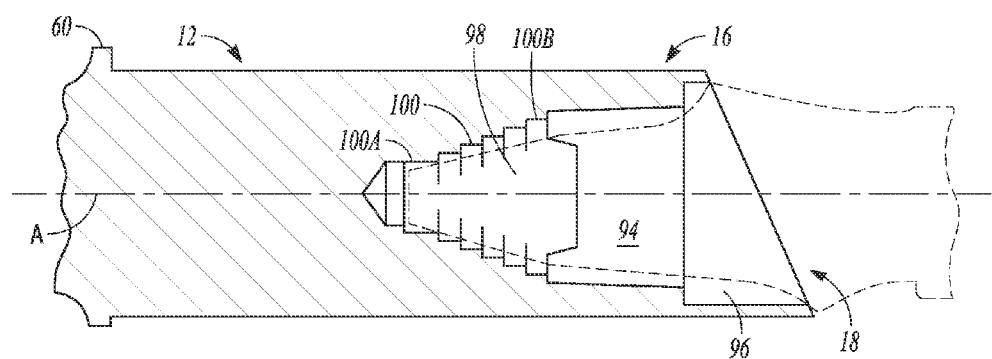
FIG. 9 is a fragmentary cross-sectional view of a drive tool according to a further embodiment.
Figure 14:
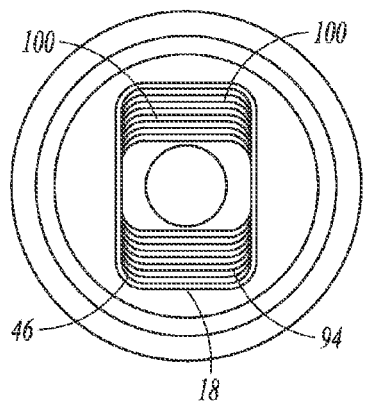
FIG. 14 is an end view of the proximal end of the drive tool of FIG. 9.
Figure 12:
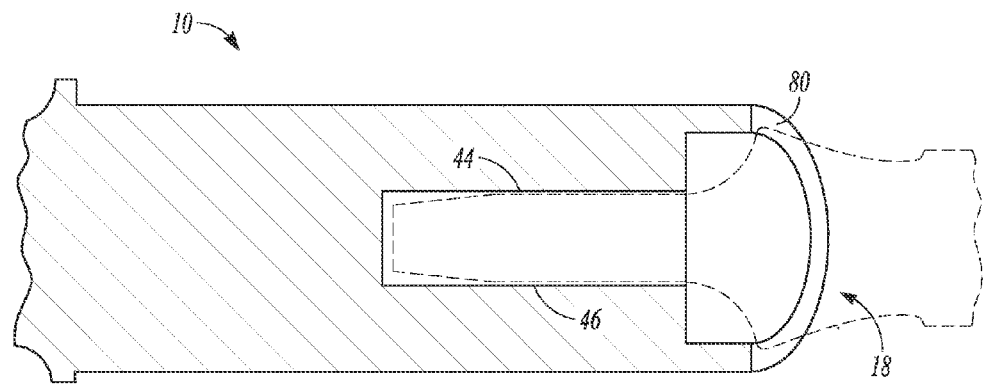
FIG. 12 is a fragmentary cross-sectional view of the drive tool of FIG. 5.

FIGS. 9 and 14 depict drive tool 92 according to another embodiment. Except as described below, drive tool 92 of FIG. 9 is substantially identical to drive tool 10 of FIGS. 1-3 discussed above, and identical reference numerals will be used to designate identical or substantially identical features therebetween. Drive tool 92 includes elongate body 12 having proximal end 14 with opening 18 defining a cavity 94, which may include drive surfaces, such as drive surfaces 44 and 46 of drive tool 10, for engaging corresponding drive surfaces of the dental implants. Cavity 94 is divided into two portions, including proximal portion 96 and distal portion 98.

Distal portion 96 of cavity 94 of drive tool 92 is further defined by a plurality of wall sections 100 defining progressively decreasing interior volumes from the proximal end 16 towards the distal end 14 of drive tool 92. Wall sections 100 have a stepped configuration defining perimeters that are substantially similar to the dimensions of head portion 36 of dental implant 22, shown in FIG. 10, and the longitudinal axes of some of wall sections 100 may be shaped to be offset from the longitudinal axes of other wall sections 100 in order to more closely dimension cavity 94 to conform to the profile of the head portion of an implant. For example, in FIG. 9, wall section 100A is offset from longitudinal axis A of drive tool 92, while wall section 100B which is substantially aligned with longitudinal axis A. This allows for cavity 94 of drive tool 92 to accept an orthopedic screw having a specific angular orientation of the head portion with respect to the body portion of the dental implant, such as dental implant 22 as described above. In this manner, wall sections 100 define an interior configuration of cavity 94 which is dimensioned to closely receive head portion 36 of implant 22 to maintain the alignment and positioning of head portion 36 of implant 22 within cavity 94.

Figure 13:
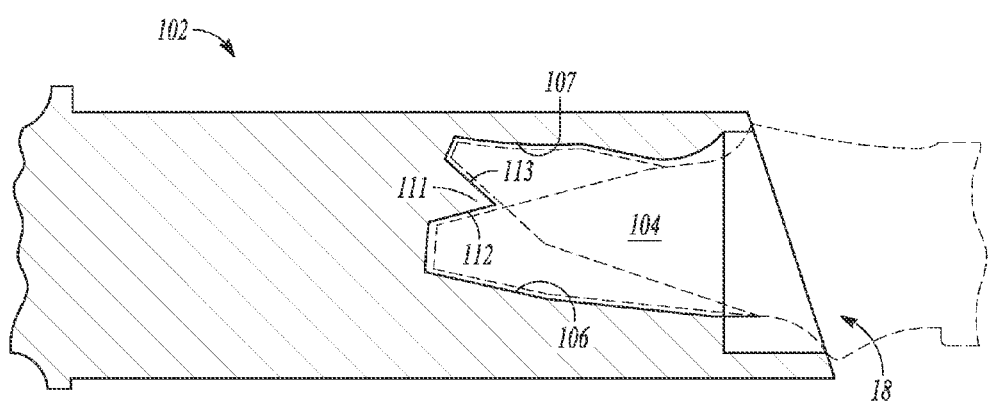
FIG. 13 is a fragmentary cross-sectional view of a drive tool according to a still further embodiment.

FIG. 13 depicts another exemplary embodiment as drive tool 102. Except as described below, drive tool 102 of FIG. 13 is substantially identical to drive tool 10 of FIG. 1 discussed above, and identical reference numerals will be used to designate identical or substantially identical features therebetween. Drive tool 102 is formed by elongate body 12 having proximal end 14 with opening 18 defining cavity 104. Cavity 104 is further defined by interior walls defining first and second portions 106 and 107 of cavity 104 having internal shapes that are substantially identical to the exterior profiles of head portions 36 and 38 of dental implants 22 and 24, respectively, with first and second portions 106 and 107 of cavity 104 terminating in frustoconical shapes substantially similar to tips 108, 110 of dental implants 22, 24, respectively. A wall 111, including a first side 112 and a second side 113, can be located between first portion 106 and second portion 107. In this manner, cavity 104 may lack drive surfaces 44 and 46, wherein rotational torque is imparted to head portions 36 and 38 of dental implants 22 and 24 via the geometric fit between first and second portions 106 and 107 of cavity 104 and head portions 36 and 38 of dental implants 22 and 24, respectively.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:
1. A drive tool for rotatably driving one of at least two dental implants, the dental implants having head portions divergent from one another, said drive tool comprising:
   a body defining a longitudinal axis, a proximal end, a distal end, and a surface extending between the proximal end and the distal end;
   a drive fitting at the distal end, the drive fitting comprising one of an internal and an external polygonal fitting;
   a cavity for receiving one of the at least two dental implants, the cavity defined within the proximal end, the cavity comprising a wall defining a first cavity portion having a cross section extending collinearly with the longitudinal axis, the cavity further comprising a second cavity portion having a cross section extending at an acute angle relative to the longitudinal axis, the second cavity portion comprising an opening on the surface;
   at least on flat driving surface in the first cavity portion for non-rotatably engaging one of the at least two dental implants;
   a coronal wall at a coronal end of the first cavity portion extending perpendicularly to the longitudinal axis; and
   an acute wall in the second cavity portion extending at an acute angle to the opening.
2. The drive tool of claim 1, wherein the first cavity portion is configured to receive a dental implant with a straight head portion.

3. The drive tool of claim 2, wherein the first cavity portion closely conforms to an outer profile of the straight head portion.

4. The drive tool of claim 2, wherein the first cavity portion is arranged so that relative rotation of the dental implant and the body is substantially limited when the straight head portion of the dental implant is positioned in the first cavity portion.

5. The drive tool of claim 2, wherein the straight head portion comprises an abutment portion.

6. The drive tool of claim 1, wherein the second cavity portion is configured to receive a dental implant with an angled head portion.

7. The drive tool of claim 6, wherein the second cavity portion closely conforms to an outer profile of the angled head portion.

8. The drive tool of claim 6, wherein the second cavity portion is arranged so that relative rotation of the dental implant and the body is substantially limited when the angled head portion of the dental implant is positioned in the second cavity portion.

9. The drive tool of claim 6, wherein the angled head portion comprises an abutment portion.

10. The drive tool of claim 1, wherein the at least one flat driving surface in the first cavity portion comprises at least one pair of flat, opposing, parallel driving surfaces.

11. The drive tool of claim 1, wherein the drive fitting comprises an internal polygonal fitting including six substantially flat walls that together define a hexagonal cross section.

12. The drive tool of claim 11, wherein the internal polygonal fitting includes a broach relief formed therein.

13. The drive tool of claim 1, wherein the drive fitting comprises an external polygonal fitting including four substantially flat walls that together define a square cross section.

14. The drive tool of claim 1, wherein the body further comprises an annular collar disposed adjacent to the drive fitting.

15. The drive tool of claim 14, wherein the body further comprises an annular flange spaced from the annular collar, the annular flange and the annular collar defining sidewalls of an annular groove formed around at least a portion of the body.

16. The drive tool of claim 15, wherein at least one of the annular flange and the annular collar includes a flat section configured to provide a visual indication when the drive tool is correctly aligned with one of the at least two dental implants.

* * * * *

UNITED STATES PATENT AND TRADEMARK OFFICE
CERTIFICATE OF CORRECTION

| | | |
|---|---|---|
| PATENT NO. | : 8,771,285 B2 | Page 1 of 1 |
| APPLICATION NO. | : 11/532291 | |
| DATED | : July 8, 2014 | |
| INVENTOR(S) | : Donahoe et al. | |

It is certified that error appears in the above-identified patent and that said Letters Patent is hereby corrected as shown below:

In the Claims

In column 6, line 58, in Claim 1, delete "on", and insert --one--, therefor.

Signed and Sealed this
Fourteenth Day of October, 2014

Michelle K. Lee
*Deputy Director of the United States Patent and Trademark Office*